US00PP10934P

United States Patent [19]

Olesen et al.

[11] Patent Number: Plant 10,934

[45] Date of Patent: Jun. 1, 1999

[54] MINIATURE ROSE VARIETY 'POULLAK'

[75] Inventors: L. Pernille Olesen; Mogens N. Olesen, both of Fredensborg, Denmark

[73] Assignee: Poulsen Roser ApS, Fredensborg, Denmark

[21] Appl. No.: 08/828,293

[22] Filed: Mar. 21, 1997

[51] Int. Cl.[6] ..... A01H 5/00

[52] U.S. Cl. ..... Plt./121

[58] Field of Search ..... Plt./9, 121

[56] References Cited

PUBLICATIONS

UPOV–ROM, 1997/04, Plant Variety Database, GTI Jouve Retrieval Software, citations for 'POULlak'.

*Primary Examiner*—Howard J. Locker

[57] ABSTRACT

A new pink blend miniature rose plant which has abundant non-fading flowers and excellent keepability. The variety successfully propagates from softwood cuttings and is suitable for year round production in commercial glasshouses. This new and distinct variety has shown to be uniform and stable in the resulting generations from propagation.

2 Drawing Sheets

SUMMARY OF THE INVENTION

The present invention constitutes a new and distinct variety of miniature rose plant which was developed by artificially crossing an un-named seedling with 'POULvic', a patented variety described and illustrated in U.S. Plant Pat. No. 8,012. The two parents were crossed and the resulting seeds were planted in a controlled environment. The new variety is named 'POULlak'.

The objective of the hybridization of this rose variety for commercial greenhouse culture was to create a new and distinct variety with:

1. Uniform and abundant flowers with excellent keepability;
2. Attractive long lasting foliage and compact growth,
3. Year-round flowering under glasshouse conditions;
4. Suitability for production from softwood cuttings in pots;
5. Durable flowers and foliage which make the variety suitable for distribution in the floral industry.

This combination of qualities was not present in previously available commercial cultivars of this type and distinguish 'POULlak' from all other varieties of which we are aware.

The seeds from the hybridization were planted in a controlled environment and evaluations were conducted of the resulting rose plants. 'POULlak' was selected by L. Pernille and Mogens N. Olesen in their rose development program in Fredensborg, Denmark in June, 1992.

Asexual reproduction of 'POULlak' by cuttings was first done by L. Pernille and Mogens N. Olesen in August, 1992. This initial and subsequent propagations have demonstrated that the characteristics of 'POULlak' are true to type and are transmitted from one generation to the next.

BRIEF DESCRIPTION OF THE DRAWINGS

The accompanying color illustrations show as true as is reasonably possible to obtain in color photographs of this type, the typical characteristics of the buds, flowers, leaves, stems, and a plant of 'POULlak'.

Specifically illustrated in SHEET 1:

1. Entire plant showing branching and the attachment of leaves, buds, and peduncles;
2. Flower bud, partially opened bud, and open bloom;

3. Flower petals, detached;
4. Sepals, receptacle, and pedicel;
5. Flowering stem with terminal bud, as well as a bare stem exhibiting thorns; and
6. Leaves.

Specifically illustrated in SHEET 2 is an entire blooming plant in a 10 cm pot.

DETAILED DESCRIPTION OF THE VARIETY

The following is a detailed description of 'POULlak', as observed in its growth in greenhouses in Fredensborg, Denmark and Half Moon Bay, Calif. and in field nursery in Applegate, Oreg. Color references are made using The Royal Horticultural Society (London, England) Colour Chart, 1995.

For a comparison, the nearest existing rose variety is 'POULoral', a patented variety described and illustrated in U.S. Plant Pat. No. 9,018. 'POULlak' is a significant improvement over 'POULoral', in that it has many more flower buds per plant. Chart 1 details several physical characteristics of 'POULlak' and the comparison variety.

CHART 1

| Characteristic | 'POULlak' | 'POULoral' |
|---|---|---|
| Thorns | Moderate | Few |
| Color of middle zone of upper side of flower petal | RHS 49 A, of the Red Group | RHS 41C of the Red Group |
| Color of petal margin, upper side of petal | RHS 49D of the Red Group | RHS 41C of the Red Group |

Parents: Un-named seedling and POULvic.

Classification:

*Botanical.*—*Rosa hybrida.*

*Commercial.*—Miniature.

Flower and Flower Bud

Blooming cycle: Recurrent.

Flower bud:

*Size.*—12–15 mm in length.

*Bud form.*—Pointed to ovoid.

*Bud color.*—R.H.S. 39 D of the red group, at ¼ opening.

*Sepals.*—R.H.S. 139 B of the green group, with weak foliaceous appendages on three of the five sepals. Margins of these three sepals also have thicker hairs. Surfaces of all sepals are moderately pubescent.

*Peduncle.*—Surface: Smooth above with stiff hairs present at the base. Length: 25–40 mm Color: Medium green. Prickles: None. Peduncle surface has limited numbers of hairs.

*Receptacle.*—Surface: Smooth and glabrous. Shape: Urned shaped. Size: Small. 4 mm×4 mm. Color: R.H.S. 141 C of the green group.

*Borne.*—Generally multiple buds, with two to four flower buds per flowering stem.

Flower bloom:

*Diameter.*—Small. 35 mm. on average.

*Form.*—Upon opening, form is a flattened convex. Completely open, the form is convex.

*Petalage.*—Double. Average range: 30–40, plus 5–10 petaloids per bloom.

*Color.*—The open bloom exhibits a blend of pinks. Upon opening, the upper surface of the petal is R.H.S. 49 A of the red group. Center petals on open flower tends to be lighter in color than exterior petals. Upon opening, the reverse side of the petal is R.H.S. 39 D of the red group. After opening, the upper surface of the petal is R.H.S. 49 B of the red group, with completely open flowers fading to 49C. After opening, the reverse surface of the petal is R.H.S. 38 C of the red group. Petal has pale yellow basal spot on inner and outer side, R.H.S. 3 D of the yellow group.

*Reflex.*—Petals reflex backwards somewhat.

*Fragrance.*—Light.

*Duration.*—Flowers last 18–21 days on the plant and 12–15 days as a cut flower.

Reproductive organs:

*Pollen.*—Color: Yellow-orange group 22B. Limited in quantity.

*Anthers.*—Size: Small. Color: Yellow-orange group 22B.

*Filaments.*—Color: Yellow-green group 150D.

*Stigmas.*—Color: Yellow-green group 150D. Superior in position to anthers.

*Styles.*—Color: Yellow-green group 149D.

*Ovaries.*—Inferior.

Plant

Plant growth: Bushy and compact. When grown as a 10 cm pot plant, the average height of the plant itself is 16–20 cm and the average width is 18–20 cm. When grown as a nursery plant on its own roots the average plant height is 25–35 cm and the average plant width is 30–40 cm.

Stems:

*Color.*—Young wood: Green. Yellow-green group 146C. Young shoots show little or no anthocyanin coloration. Older wood: Green. R.H.S. 147 C of the yellow-green group.

*Thorns.*—Incidence: Moderate number. Size: Average length: 3–4 mm. Color: Between Greyed-red group 179D and Greyed-orange 174D.

Plant foliage: Normal number of leaflets on average leaves: 5 leaflets.

*Leaf size.*—Small. 60 mm×30 mm.

*Abundance.*—Above average.

*Color, mature foliage.*—Upper leaf surface: Dark green. R.H.S. 147 A of the yellow-green group. Lower leaf surface: Medium green. R.H.S. 147 C of the yellow-green Color group.

*Color, Juvenile foliage.*—Margins of expanding juvenile leaflets, petioles, and stipules have red intonation of greyed-red group 180A. Juvenile foliage is green group 143B. The lower leaf surface is green group 147C.

Plant leaves and leaflets:

*Stipules.*—Present. To 10 mm in length. Hairs present on margins. Color between yellow-green group 147B.

*Petiole.*—Length: 8–10 mm. Underneath: With hairs and prickles. Color: Yellow-green group 147B.

*Edge.*—Moderately serrated.

*Shape.*—Leaflets are ovate.

*Rachis.*—With hairs and prickles. Color: Yellow-green group 147B.

*Leaflets.*—Number on an average leaf on the mid portion of the plant: 5.

*Texture.*—Matte finish. Thin texture.

Disease resistance: Resistant to blackspot, rust, and Botrytis diseases under normal growing conditions.

We claim:

1. A new and distinct variety of rose plant of the miniature class, substantially as herein illustrated and described as a distinct and novel rose variety due to its uniform and abundant flowers with excellent keepability, attractive long lasting foliage and compact growth, ability to flower year-round under glasshouse conditions, suitability for production from softwood cuttings in pots, and its durable flowers and foliage which make the variety suitable for distribution in the floral industry.

* * * * *

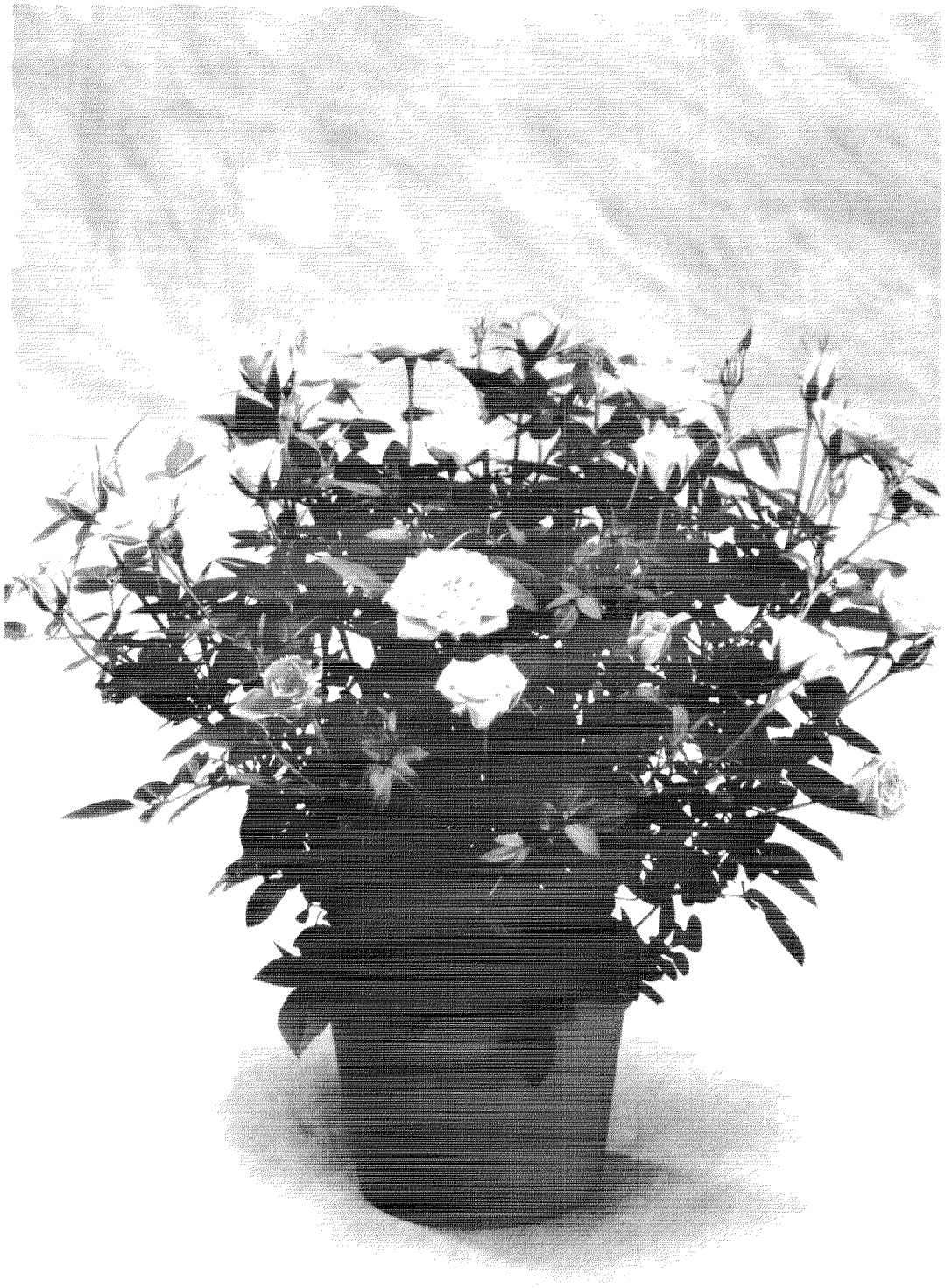

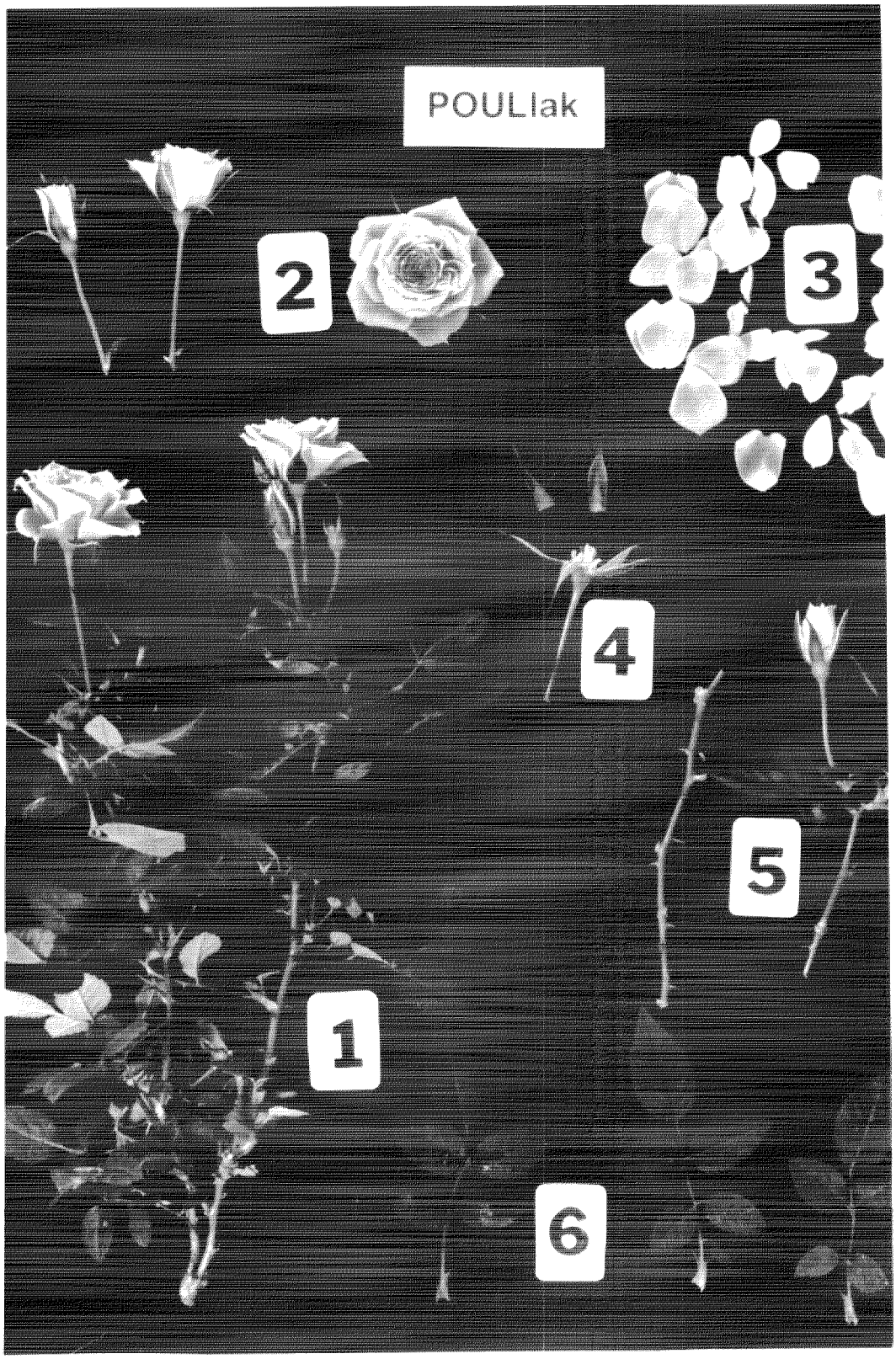
POULlak
2
3
4
5
1
6